United States Patent [19]

Drent

[11] Patent Number: 5,210,280

[45] Date of Patent: May 11, 1993

[54] PROCESS FOR THE PREPARATION OF ALKANEDIOIC ACID DERIVATIVES

[75] Inventor: Eit Drent, Amsterdam, Netherlands

[73] Assignee: Shell Oil Company, Houston, Tex.

[21] Appl. No.: 837,132

[22] Filed: Feb. 19, 1992

[30] Foreign Application Priority Data

Mar. 12, 1991 [GB] United Kingdom ................ 9105211

[51] Int. Cl.$^5$ ...................... C07C 67/38; C07C 51/12; C07C 51/14; C07C 231/00

[52] U.S. Cl. ................................... 560/204; 549/231; 549/233; 554/68; 554/113; 554/129; 558/353; 558/441; 558/443; 560/190; 560/193

[58] Field of Search ...................... 560/204, 190, 193; 554/68, 113, 129; 558/353, 441, 443; 562/517, 590, 606, 607, 890, 891; 564/132; 549/231, 233

[56] References Cited

U.S. PATENT DOCUMENTS

| | | | |
|---|---|---|---|
| 4,281,174 | 7/1981 | Current | 560/204 |
| 4,414,409 | 11/1983 | Waller | 560/233 |
| 4,843,144 | 6/1989 | Van Broekhoven et al. | 528/392 |

FOREIGN PATENT DOCUMENTS

| | | |
|---|---|---|
| 0143911 | 6/1985 | European Pat. Off. . |
| 0231044 | 8/1987 | European Pat. Off. . |
| 277695 | 2/1988 | European Pat. Off. . |
| 283092 | 3/1988 | European Pat. Off. . |
| 296687 | 6/1988 | European Pat. Off. . |
| 298540 | 6/1988 | European Pat. Off. . |
| 0274795 | 7/1988 | European Pat. Off. . |
| 0305012 | 3/1989 | European Pat. Off. . |
| 58-72539 | 4/1983 | Japan . |
| 89/276193 | 9/1989 | Netherlands . |
| 89/291236 | 9/1989 | Netherlands . |
| 2183631 | 6/1987 | United Kingdom . |
| 2202165A | 9/1988 | United Kingdom . |

Primary Examiner—José G. Dees
Assistant Examiner—Vera C. Clarke

[57] ABSTRACT

A process for the preparation of alkanedioic acid derivatives comprising reacting an alkenoic acid derivative with carbon monoxide and a nucleophilic compound having a mobile hydrogen atom in the presence of a catalyst system comprising a source of a Group VIII metal, a source of a bidentate diphosphine liquid, a source of an anion and a source of a quinone promoter.

10 Claims, No Drawings

PROCESS FOR THE PREPARATION OF ALKANEDIOIC ACID DERIVATIVES

FIELD OF THE INVENTION

This invention relates to the monocarbonylation of olefinically unsaturated compounds, and in particular to a process for the preparation of alkanedioic acid derivatives by the carbonylation of an alkenoic acid having a mobile hydrogen atom.

BACKGROUND OF THE INVENTION

It is known that reactions of the above type are catalyzed by a Group VIII metal such as cobalt. For example, EP-A-143911 discloses the preparation of succinic diesters starting from an acrylic ester and using a cobalt carbonyl complex as catalyst. This known process suffers from the disadvantage of requiring rather severe reaction conditions, such as a carbon monoxide pressure of 120-130 bar. A further process using a cobalt catalyst is described in JP-A-83/72539.

In EP-A-274795, a process is described for the carbonylation of olefinically unsaturated compounds with a palladium catalyst. The exemplified catalyst systems comprise a source of palladium, a triarylphosphine, a strong acid and a stabilizer, such as phosphine oxides and sulfides, or tertiary acids. According to its specification, the olefinic substrate may be substituted with a broad class of functional groups, including acid, ester, acid amide and acid nitrile groups, but no experimental data on the achievable conversions and selectivities are given.

It has now been found that alkanedioc acid derivatives can be prepared under mild conditions by carbonylation, if use is made of a specific catalyst system. Using this catalyst system, good conversions and excellent selectivities to the desired products are obtained.

SUMMARY OF THE INVENTION

The present invention therefore provides a process for the preparation of alkanedioic acid derivatives by carbonylation of an alkenoic acid derivative by reaction with carbon monoxide and a nucleophilic compound having a mobile hydrogen atom in the presence of a catalyst system comprising a source of a Group VIII metal, a source of a bidentate diphosphine ligand, a source of an anion and a source of a promoter.

DESCRIPTION OF THE PREFERRED EMBODIMENTS

Suitable substrates for the present process include alkenoic acids, alkenoic acid anhydrides, alkenoic acid amides, alkenoic acid nitriles, and alkenoic esters. Preferably, the substrate has the acid functionality directly attached to an olefinic carbon atom, and thus is a 2-alkenoic acid derivative. The alkenyl moiety of the alkenoic acid may be substituted, but is preferably unsubstituted, such as in vinyl, 1-propenyl, 1-butenyl, 1-pentenyl and 1-hexenyl, and preferably has from 2 to 12 carbon atoms. Representative examples of suitable substrates include acrylic acid, methacrylic acid, 2-butenoic acid, 2-pentenoic acid, acrylonitrile, methacrylonitrile, acrylamide, and methacrylamide. Further examples of substrates include N-substituted acrylamides and methacrylamides, acrylates, methacrylates, and other esters of the afore-mentioned alkenoic acids. The N-substituents of the amide groups and the O-substituents of the ester groups may be aliphatic, cycloaliphatic or aromatic, and may be substituted or unsubstituted, and preferably have from 1 to 10 carbon atoms. Examples are methyl acrylate, ethyl acrylate, phenyl acrylate, i-propyl acrylate, n-butyl acrylate, and the corresponding methacrylates, and N,N-dimethylacrylamide. Preferably, the substrate alkenoic ester derivative is an alkenoic acid, more preferably an acrylic ester.

The nucleophilic compound having a mobile hydrogen atom used in the process of the invention can be an alcohol, which is preferred, an acid, an amine or water. Together with a molecule of carbon monoxide absorbed in the carbonylation reaction, the use of an alcohol will introduce an ester group in the product of the carbonylation reaction; the use of an acid will introduce an anhydride group; the use of an amine will introduce an amide group; and the use of water will introduce an acid group, according to the overall reaction:

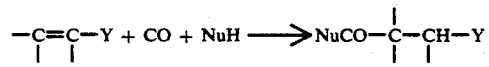

wherein Y represents the acid function of the starting alkenoic acid derivative, and Nu represents the remnant moiety of the nucleophilic compound after removal of the mobile hydrogen atom. Suitable alcohols, acids, or amines may be aliphatic, cycloaliphatic or aromatic, and may be substituted or unsubstituted. Representative examples include methanol, ethanol, propanol, butanol, phenol, acetic acid, stearylalcohol, benzylalcohol, cyclohexanol, cresol, propionic acid, butyric acid, pivalic acid, aniline, and p-anisidine. Preference is given to nucleophilic compounds having 1 to 12 carbon atoms.

It will be appreciated that the NuCO function formed may be the same as the function Y of the precursor, such as in dimethylsuccinate obtained from the carbonylation of methyl acrylate in the presence of methanol, or may be the same type, as in ethylmethylsuccinate obtained either from the carbonylation of methylacrylate in the presence of ethanol, or from the carbonylation of ethyacrylate in the presence of methanol.

NuCO and Y may also be different types of acid functions, such as in monomethylsuccinate obtained from the carbonylation of methacrylate in the presence of water. The skilled man will appreciate that the alternative route of carbonylation of acrylic acid in the presence of methanol may be liable to competitive reactions involving the acrylic acid itself functioning as nucleophilic compound NuH, with consequent decrease of selectivity. Preferably, the reactants are selected such that the nucleophilic compound is more reactive than the acid function of the alkenoic acid derivative in order to suppress the occurrence of such competitive reactions.

Examples of Group VIII metals are iron, cobalt, nickel, ruthenium, rhodium, palladium, iridium, and platinum. The catalyst system to be used in the process according to the invention preferably comprises a source of palladium. The source of Group VIII metal may be, for example, the metallic element or a compound of the Group VIII metal. The source of a Group VIII metal is preferably a compound of the Group VIII metal, most preferably a compound of palladium.

Examples of compounds of Group VIII metals include salts, for example, sats of nitric acid, sulphuric acid, carboxylic acids such as alkane carboxylic acids having not more than 12 carbon atoms; e.g. acetic acid, and hydrohalic acids. Since halic ions can be corrosive, salts of hydrohalic acids are not preferred. Other examples of compounds of Group VIII metals include complexes, such as complexes with acetylacetonate, phosphines, and/or carbon monoxide. For example, the compound of a Group VIII metal may be palladium acetylacetonate, tetrakistriphenylphosphinepalladium, bis-tri-o-tolylphosphinepalladium acetate, or 1,3-bis(diphenylphosphino)propanepalladium acetate.

The catalyst system used in the present process further comprises a bidentate phosphine liquid. Any phosphine having at least two phosphine P atoms at intramolecular distance and configuration allowing coordination to a single metal atom is suitable. Accordingly, any bridge connecting said at least two phosphorus atoms should be free of any substituents causing hindrance to metal coordination. Suitable and readily accessable bidentate diphosphine ligands can have the general formula $R^1R^2P—X—PR^3R^4$ wherein X represents a substituted or unsubstituted alkylene or oxaalkylene group, and each of $R_1$, $R_2$, $R_3$ and $R_4$ independently represents a substituted or unsubstituted alkyl, aryl or N-heteroaryl group. The bridging group X preferably has from 2 to 8 atoms in the bridge. The groups $R_1$, $R_2$, $R_3$ and $R_4$ preferably each have from 1 to 12 carbon atoms.

Examples of bidentate diphosphine ligands include 1,3-bis(diphenylphosphino)propane, 1,4-bis(diphenylphosphino)butane, and 1,5-bis(di-o-tolylphosphino)-3-oxapentane. Preferably, the groups $R_1$, $R_2$, $R_3$ and $R_4$ are aliphatic and examples of preferred bidentate diphosphine ligands include tetraalkyl alkylenediphosphines such as 1,3-bis(dimethylphosphino)propane, 1,3-bis(di-i-propylphosphino)propane, 1,3-bis(di-n-butylphosphino)propane, and 1,4-bis(di-n-butylphosphino)butane.

The catalyst system used in the present process also comprises a source of anions. The source of anion may be the associated acid or a salt thereof, in particular a salt of a transition metal such as nickel or copper. It will be appreciated that a Group VIII metal salt may constitute a source for both the Group VIII metal and the anion components of the presently used catalyst system. The anion preferably is non-coordinating to the Group VIII metal, by which is meant that little or no covalent interaction occurs between the Group VIII metal and the anion. Without wishing to be bound by any theory, it is believed that the catalytically active species in the present process is a cationic Group VIII metal complex comprising non-coordinating anion(s). Typical examples of such anions are $PF_6^-$, $SbF_6^-$, $BF_4^-$, and $ClO_4^-$, and anions derived from an acids having a pKa below 2 (measured at 18° C. in aqueous solution), such as sulfuric acid, sulfonic acids, e.g. a substituted or unsubstituted hydrocarbylsulfonic acid such as benzenesulfonic acid, p-toluenesulfonic acid, naphthalenesulfonic acid, a substituted or unsubstituted alkylsulfonic acid such as methanesulfonic acid, tertbutylsulfonic acid, 2-hydroxypropanesulfonic acid or trifluoromethanesulfonic acid, chlorosulfonic acid or fluorosulfonic acid, phosphonic acids and carboxylic acids such as trichloroacetic acid or trifluoroacetic acid. The source of anions may also be an acidic ion exchange resin, for example a sulfonated ion exchange resin.

The presently used catalyst system further comprises a promoter, suitably an organic oxidant promoter, such as quinones and nitro compounds. While not wishing to be bound by theory, it is believed that the promoter activates the catalytic palladium center by annihilating any hydrides or hydrogen generated through a shift reaction from traces of water present in the system. Suitable quinones comprise the ortho- or para-diketo benzene moiety, which may be substituted or be part of a condensed ring system. Examples of suitable quinone promoters include benzoquinones, such as 1,2-benzoquinone, 1,4-benzoquinone, 2-chloro-1,4-benzoquinone, 2,6-dimethyl-1,4-benzoquinone and tetrachloro-p-benzoquinone, naphthoquinones, such as 1,2-naphthaquinone and 1,4-naphthaquinone, anthraquinones, such as 9,10-anthraquinone, and phenanthroquinones such as 9,10-phenanthroquinone. Mixtures of quinones can also be present.

As used hereinbefore, an alkyl group, as such or in an alkoxy or acyl group, is preferably a $C_{1-10}$ alkyl group, more preferably a $C_{1-6}$ alkyl group. Examples of alkyl groups are methyl, ethyl, n-propyl, iso-propyl, n-butyl, iso-butyl and tert-butyl. An aryl group is preferably a phenyl or a naphthyl group. A cycloalkyl group is preferably a $C_{3-6}$ alkyl group, for example, cyclopentyl or cyclohexyl. An N-heteroaryl group represents an aromatically unsaturated ring containing an imino nitrogen atom. It is preferably a 6-membered ring containing one, two or three nitrogen atoms, such as pyridyl, pyrazinyl, quinolyl, isoquinolyl, pyrimidinyl, pyridazinyl, cinnolinyl, triazinyl, quinoxalinyl, and quinazolinyl groups. When a group is said to be "substituted" in this specification, it may be substituted by one or more substituents selected from the group including halogen atoms, alkyl groups, alkoxy groups, haloalkyl groups, haloalkoxy groups, acyl groups, acyloxy groups, amino groups, hydroxyl groups, nitrile groups, acylamino groups, and aryl groups.

The catalyst system used in the process according to the invention may be homogeneous or heterogeneous. Preferably, it is homogeneous.

The ratio of the number of moles of bidentate diphosphine per gram atom of Group VIII metal is not critical. Preferably, it is in the range of from 0.5 to 5, more preferably in the range of from 1 to 2. The ratio of moles of anions per gram atom of Group VIII metal is not critical. Preferably, it is in the range of from 0.5 to 100, more preferably in the range of from 1 to 10. The ratio of moles of quinone promoter is not critical. Preferably, it is in the range of from 1 to 1000, more preferably in the range of from 5 to 100.

The process according to the invention is conveniently effected in the liquid phase. Excess of one of the reactants may be used to serve as a solvent and thus maintain the reaction mixture as a liquid phase. A separate solvent is not essential. Solvents suitable for use in the process according to the invention include for example, sulfoxides and sulfones, for example dimethylsulfoxide and tetrahydrothiophene-2,2-dioxide, aromatic hydrocarbons such as benzene, toluene, and xylenes, esters such as methyl acetate butyrolacetone, and ethers such as anisole, 2,5,8-trioxanonane, diphenylether and diisopropylether.

The process according to the invention is conveniently effected at a temperature in the range of from about 20° C. to about 200° C., more conveniently from about 50° C. to about 125° C.

The process according to the invention is preferably effected at a pressure of from about 1 to about 100 bar. Pressures higher than about 100 bar may be used, but are generally economically unattractive due to special apparatus requirements.

The molar ratio of the alkenoic acid derivative to the nucleophilic compound having a mobile hydrogen atom may vary between wide limits, in particular when either is used as solvent, and will generally be in the range of from about 0.01 to about 100:1.

The quantity of the Group VIII metal is not critical. Preferably quantities are used within the range $10^{-7}$ to $10^{-1}$ gram atom Group VIII metal per mole of alkenoic acid derivative.

The carbon monoxide required for the process according to the invention may be used in a practically pure form or diluted with an inert gas, for example nitrogen. The presence of substantial amounts of hydrogen in the gas stream is undesirable on account of the hydrogenation of the olefinic precursor which may occur under the reaction conditions.

The process according to the invention may be carried out continuously or batchwise.

The catalyst systems used in the process according to the invention may be prepared by any method. They may be prepared by combining a separate Group VIII metal compound, the bidentate diphosphine, the source of anions, and the quinone promoter. Alternatively, they may be prepared from a Group VIII metal compound which is a complex of a Group VIII metal, the phosphine and the anion, in combination with the quinone promoter. If the catalyst system is prepared from the metallic Group VIII metal element as such, the anion is added in the form of the corresponding acid.

The reactants and catalyst components used in the present process are known compounds, and are commercially available or can be prepared by methods well established in the literature.

The invention will now be described by the following Examples which are included from illustrative purposes and are not intended to be construed as limiting the scope of the invention.

EXAMPLES 1-11

A 250 ml stainless steel autoclave equipped with a magnetic stirrer was each time charged with 20 ml methyl acrylate, 40 ml methanol, 0.25 mmol of palladium acetate and the amounts of further catalyst components as indicated in Table 1. The autoclave was then flushed with carbon monoxide, and then charged with carbon monoxide to a pressure of 40 bar. Subsequently, the autoclave was sealed and heated to a temperature as indicated for a period of 5 or 15 hours, as indicated.

After the indicated reaction time, the contents of the autoclave were analyzed by gas-liquid chromatography (GLC). The observed conversions, expressed as percentages and defined as 100 b/c, in which "b" is the total amount of methyl acrylate that has been converted and "c" is the initial amount of methyl acrylate, and selectivities, expressed as percentages and defined as 100 a/b, in which "a" is the amount of methyl acrylate that has been converted into dimethylsuccinate and "b" again is the total amount of methyl acrylate that has been converted, and represented in Table 1.

TABLE I

| Example No. | Pd(OAc)$_2$ mmol | phosphine[1] (mmol) | anion source[2] (mmol) | quinone[3] (mmol) | temperature °C. | time hour | conversion % | selectivity % |
|---|---|---|---|---|---|---|---|---|
| 1 | 0.25 | TBPD, (0.3) | NiTFS, (0.5) | NQ, (5) | 100 | 5 | 30 | 99 |
| 2 | 0.25 | TBPD, (0.3) | NiTFS, (0.5) | NQ, (5) | 115 | 5 | 45 | 99 |
| 3 | 0.25 | TBPD, (0.3) | NiTFS, (0.5) | NQ, (10) | 90 | 5 | 15 | 99 |
| 4 | 0.25 | TBPD, (0.3) | NiTFS, (0.5) | NQ, (10) | 90 | 15 | 45 | 99 |
| 5 | 0.25 | TBPD, (0.3) | TFSA, (0.5) | NQ, (5) | 100 | 5 | 20 | 94 |
| 6 | 0.25 | TEPD, (0.3) | NiTFS, (0.5) | NQ, (5) | 90 | 15 | 55 | 98 |
| 7 | 0.25 | PPh$_3$, (3.0) | PTSA, (2.0) | — | 100 | 5 | 5 | 67 |
| 8 | 0.25 | PPh$_3$, (3.0) | PTSA, (2.0) | — | 100 | 15 | 7 | 67 |
| 9 | 0.25 | PPh$_3$, (3.0) | TFSA, (2.0) | NQ, (5) | 100 | 5 | 3 | 55 |
| 10 | 0.25 | TBPD, (0.3) | TFSA, (0.5) | — | 100 | 5 | <1 | n.d.[4] |
| 11 | 0.25 | TBPD, (0.3) | NiTFS, (0.5) | — | 90 | 5 | 1 | n.d. |

Notes:
[1] TBPD = 1,3-bis(di-n-butylphosphino)propane; TEPD = 1,3-bis(diethylphosphino)propane; PPh$_3$ = triphenylphosphine
[2] NiTFS = nickel di-trifluoromethylsulphonate; TFSA = trifluoromethylsulphonic acid; PTSA = p-toluenesulphonic acid
[3] NQ = 1,4-naphthoquinone
[4] n.d. = not determined Examples 1-6 are within the scope of the present invention, and show that good conversions and excellent selectivities are obtained, if a catalyst system comprising four components in accordance with the invention is used for the preparation of dimethylsuccinate by carbonylation of methyl acrylate.

In Examples 7 and 8, the catalyst system comprises a monodentate phosphine ligand and no quinone promoter. Low conversion and moderate selectivities were observed. In Example 9, the catalyst system comprises a monodentate phosphine ligand in conjunction with a quinone promoter. However, the addition of a quinone appeared to have a negative effect on the catalyst system of Examples 7 and 8.

Examples 10 and 11 show that a quinone promoter is an essential component of a catalyst system containing a bidentate diphosphine ligand.

EXAMPLE 12

Using the procedure, equipment and catalyst system of Example 1, a mixture of 20 ml acrylonitrile and 40 ml methanol was reacted at 110° C. for a period of 7 hours. According to the GLC analysis the conversion of acrylontrile was 5% with a selectivity of 99% into the monomethyl ester mononitrile of malonic acid (methyl cyanoacetate).

What is claimed is:

1. A process for the preparation of alkanedioic acid derivatives which comprises reacting at a temperature in the range of from about 40° C. to about 125° C. and a pressure in the range of from about 2 bar to about 100 bar an alkenoic acid derivative with carbon monoxide and a nucleophilic compound having a mobile hydrogen atom selected from the group consisting of an alcohol, an acid, an amine and water, in the presence of a catalyst system comprising a source of a Group VIII metal, a source of a bidentate phosphine ligand, a source of an anion selected from the group consisting of an acid and a salt of an acid and a quinone promoter.

2. The process as claimed in claim 1, wherein the alkenoic acid derivative is selected from the group consisting of an alkenoic acid, an alkenoic acid anhydride, an alkenoic acid amide, an alkenoic acid nitrile, an alkenoic ester and mixtures thereof.

3. The process as claimed in claim 2, wherein the alkenoic acid derivative is an alkenoic ester.

4. The process as claimed in claim 3, wherein the alkenoic acid derivative is an acrylic ester.

5. The process as claimed in claim 1, wherein the nucleophilic compound having a mobile hydrogen atom is an alcohol.

6. The process as claimed in claim 1, wherein the source of a Group VIII metal is a source of palladium.

7. The process as claimed in claim 1, wherein the bidentate diphosphine ligand has the formula $R^1R^2P-X-PR^3R^4$ wherein X represents a substituted or unsubstituted alkylene or oxaalkylene group, and each of $R_1$, $R_2$, $R_3$ and $R_4$ independently represents a substituted or unsubstituted alkyl, aryl or N-heteroaryl group.

8. The process as claimed in claim 7, wherein the bidentate diphosphine ligand is a tetraalkyl alkylenediphosphine.

9. The process as claimed in claim 1, wherein the anion is a non-coordinating anion which is derived from an acid having a pKa below 2.

10. The process as claimed in claim 1, wherein said quinone promoter is selected from the group consisting of benzoquinones, naphthoquinones, anthraquinones, phenanthroquinones and mixtures thereof.

* * * * *